(12) United States Patent
Pinillos Martínez et al.

(10) Patent No.: US 10,408,719 B2
(45) Date of Patent: Sep. 10, 2019

(54) SYSTEM AND METHOD FOR TESTING BONDED JOINTS

(71) Applicant: AIRBUS OPERATIONS S.L., Getafe (ES)

(72) Inventors: Ricardo Pinillos Martínez, Getafe (ES); Augusto Pérez Pastor, Getafe (ES); Gema Lorena Fernández Artalejo, Getafe (ES)

(73) Assignee: AIRBUS OPERATIONS S.L., Getafe (ES)

( * ) Notice: Subject to any disclaimer, the term of this patent is extended or adjusted under 35 U.S.C. 154(b) by 114 days.

(21) Appl. No.: 15/804,053

(22) Filed: Nov. 6, 2017

(65) Prior Publication Data

US 2018/0128724 A1 May 10, 2018

(30) Foreign Application Priority Data

Nov. 7, 2016 (EP) .................................. 16382515

(51) Int. Cl.
*G01N 3/08* (2006.01)
*G01N 19/04* (2006.01)
*G01N 33/00* (2006.01)

(52) U.S. Cl.
CPC .............. *G01N 3/08* (2013.01); *G01N 19/04* (2013.01); *G01N 2033/0003* (2013.01); *G01N 2203/0091* (2013.01); *G01N 2203/026* (2013.01)

(58) Field of Classification Search
CPC .................................. G01N 3/08; G01N 19/04
See application file for complete search history.

(56) References Cited

U.S. PATENT DOCUMENTS

| | | | | |
|---|---|---|---|---|
| 5,894,981 A | * | 4/1999 | Kelly | B23K 20/004 228/104 |
| 8,621,661 B2 | * | 12/2013 | Nahm | G01N 3/066 850/44 |
| 2008/0173098 A1 | * | 7/2008 | Liu | G01N 19/04 73/827 |
| 2014/0326074 A1 | * | 11/2014 | Van Voast | G01N 19/04 73/827 |
| 2015/0276579 A1 | * | 10/2015 | Jeong | G01N 19/04 73/150 A |
| 2016/0258862 A1 | * | 9/2016 | Shin | G01N 19/04 |

FOREIGN PATENT DOCUMENTS

| | | |
|---|---|---|
| FR | 3028313 | 5/2016 |
| JP | S56111439 | 9/1981 |
| JP | 2000074819 A * | 8/1998 |
| WO | 2016001426 | 1/2016 |

OTHER PUBLICATIONS

European Search Report, dated May 12, 2017, priority document.

* cited by examiner

*Primary Examiner* — Lisa M Caputo
*Assistant Examiner* — Jamel E Williams
(74) *Attorney, Agent, or Firm* — Greer, Burns & Crain, Ltd.

(57) ABSTRACT

A system for testing bonded joints that comprises a swing tool, an actuator, pressure measuring device and a first fixing arrangement. The actuator of the system is configured to apply a compression force or a traction force on the swing tool in order to separate two elements, and the pressure measuring device is configured to measure the force applied on the swing tool. A method for testing bonded joints using the system is also provided.

12 Claims, 9 Drawing Sheets

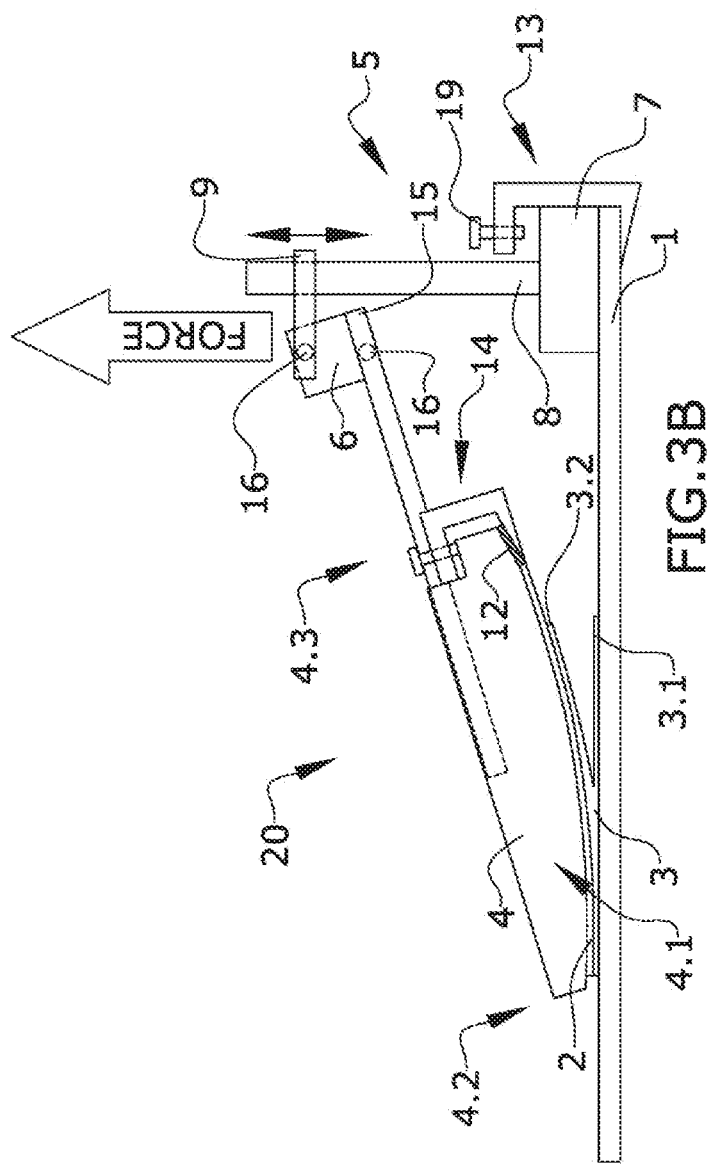

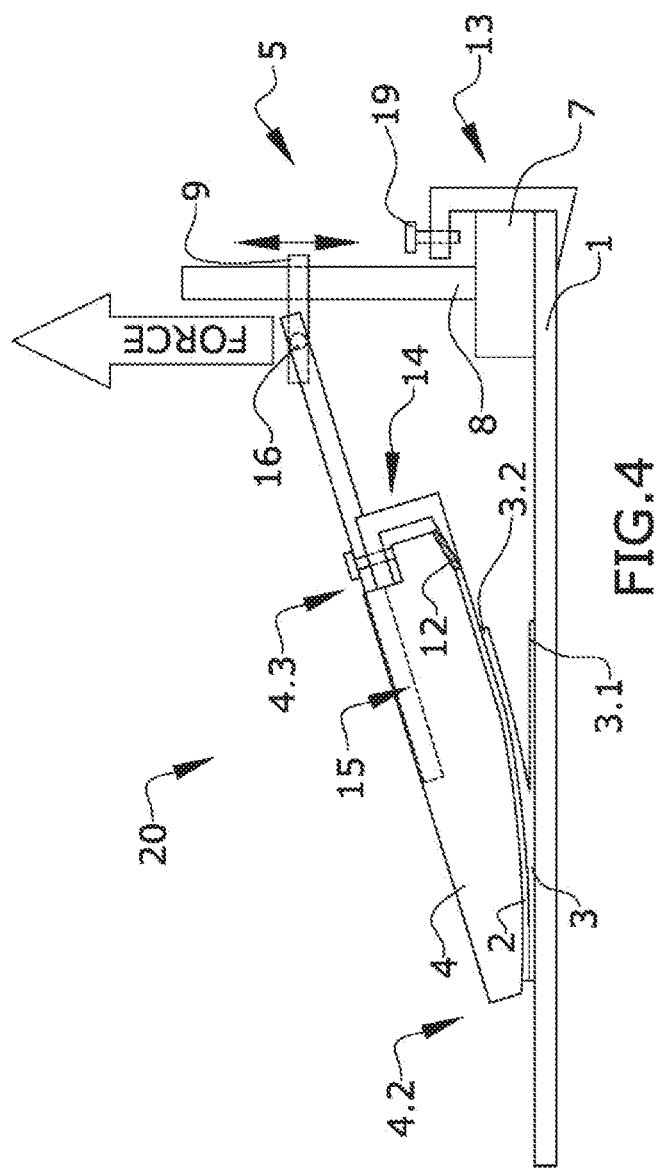

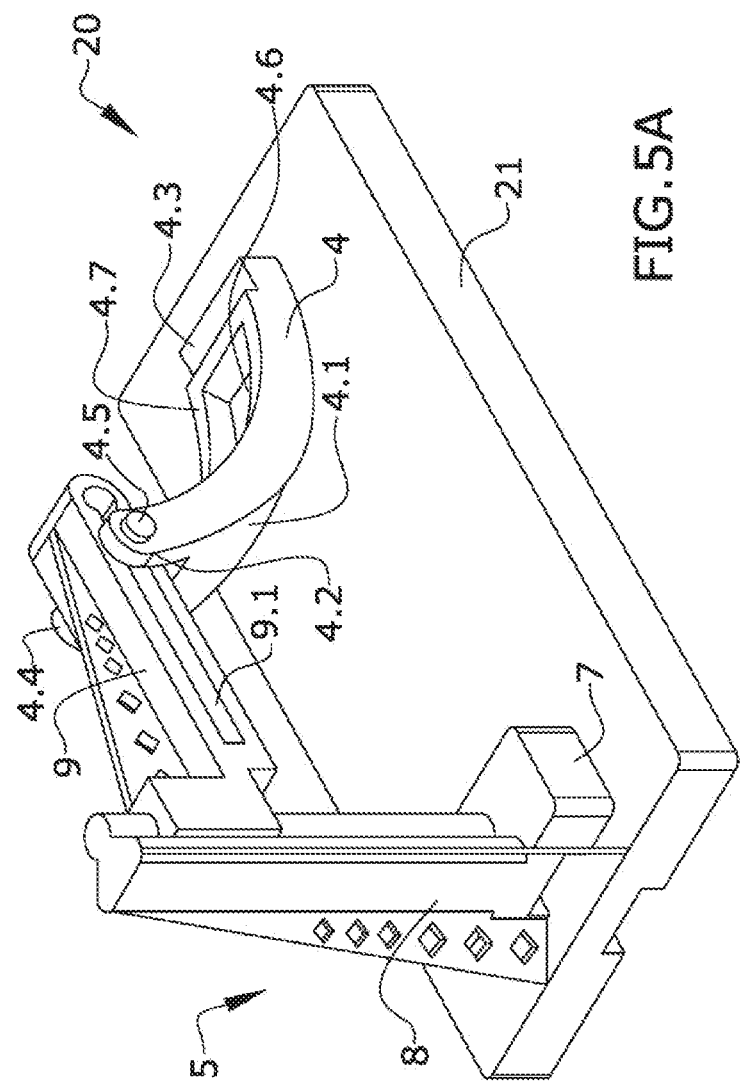

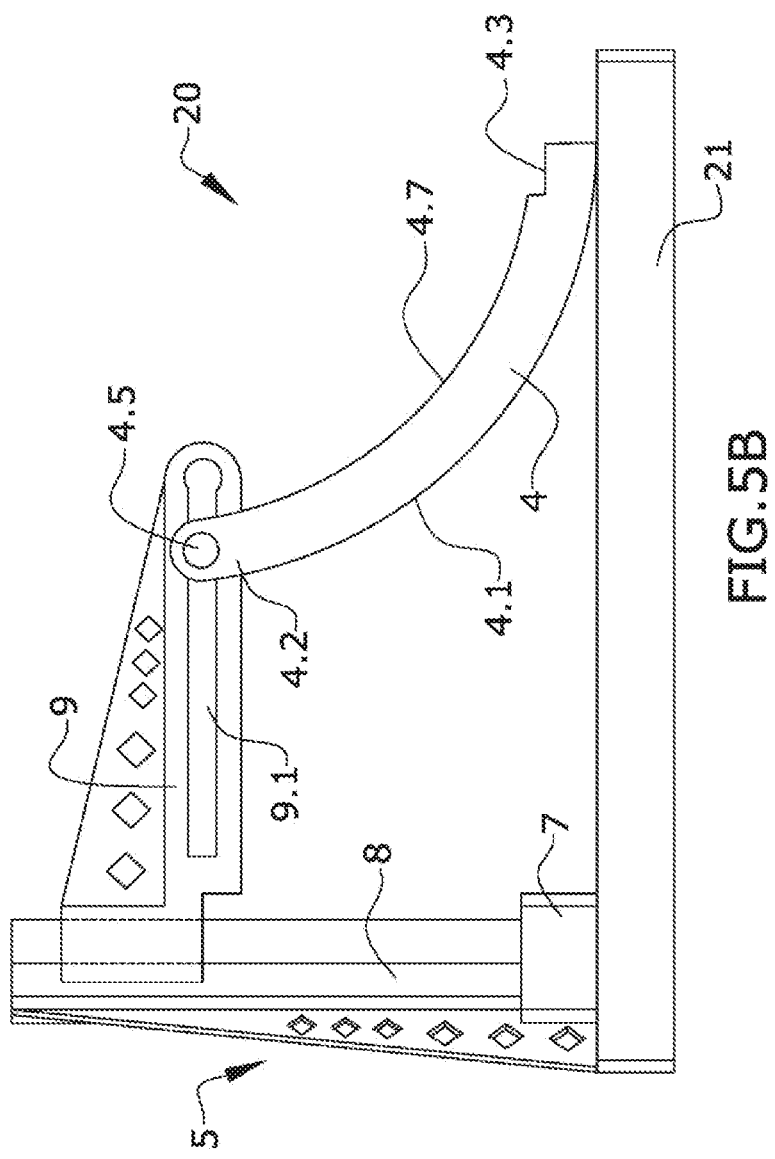

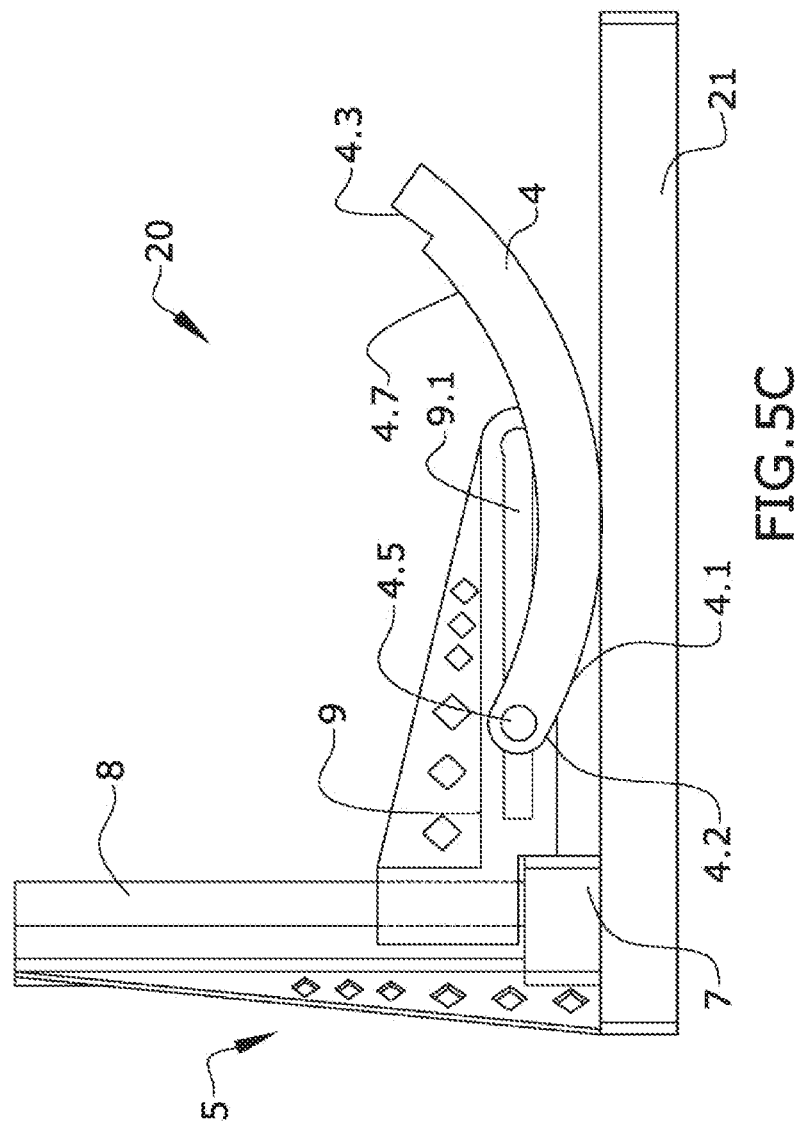

SYSTEM AND METHOD FOR TESTING BONDED JOINTS

CROSS-REFERENCES TO RELATED APPLICATIONS

This application claims the benefit of the European patent application No. 16382515.1 filed on Nov. 7, 2016, the entire disclosures of which are incorporated herein by way of reference.

TECHNICAL FIELD OF THE INVENTION

The present invention belongs to the field of structural bonded joints. Particularly, it relates to a test of the fracture toughness of bonded joints.

BACKGROUND OF THE INVENTION

The strength of structural bonded joints in aeronautical is testing by bonded tests. In the case of composite material parts, the tests are performed on the same composite materials, the same machines and the same process as the parts that are represented.

Until now, one possible method for testing bonded joints is the G1c test, which is a standard test of bonding line stress characterization. This method is carried out through calibrated testing machines in laboratories. This method consists of separating two strips of material which are bonded between them, and registering the strength and deformation.

Another method, known as Drum Peel Test, is applied for testing bonded joints. This method is focused on sandwich structures, and it consists of rolling the outer face of an element on a drum and the rolled strength and displacement of the drum is recorded.

These known methods for testing are carried out through calibrated testing machines in laboratories, and require complex machines and high method costs, and high testing times.

SUMMARY OF THE INVENTION

The present invention provide a swing tool for testing the fracture toughness of bonded joints, the tool being a simplified tool that overcome the disadvantages of the known methods.

In a first inventive aspect, the invention provides a system for testing bonded joints, the bonded joints comprising:
a first element,
a second element, and
an adhesive line located between the first and second element,
wherein the first and second element are joined together by the adhesive line, and the first and second element comprise an end side free of adhesive line between both elements,
the system comprising:
a swing tool comprising
  a first curved side configured to be located and swing on the second element,
  a first cantilevered end, and
  a support end,
an actuator,
pressure measuring means, and
a first fixing means configured to fix the swing tool to the second element,
wherein the actuator is configured to apply a force to the swing tool and configured to separate the second element with respect to the first element, and
wherein the pressure measuring means are configured to measure a force applied by the actuator to the swing tool.

Advantageously, the present system simplifies the known test methods, providing a portable and repetitive test which improves robustness and representativeness, and which reduces the complexity of the test and reduces values dispersion. The fact that the system is portable allows the system to be applied directly on a part which is the object of study, reducing lead time of the test.

Additionally, the present system allows advantageously controlling the deformation of the second element with respect to the first element during the test, thus increase the sensitivity of failure detection.

Throughout this entire document, "separate" and "detach" will be used interchangeably and understood as detaching the second element from the first element.

In a particular embodiment, the actuator comprises a motor with an axis, the motor being configured to supply power to the actuator. Additionally, the actuator comprises a horizontal bar element configured to move vertically along the axis by the motor.

Advantageously, the motor allows the movement of the actuator in such a way that it supplies power providing the movement of the horizontal bar element along the axis.

In a particular embodiment, the pressure measuring means is a load cell located in contact with the swing tool and the actuator.

In another particular embodiment, the pressure measuring means is a load cell located inside the actuator.

In a particular embodiment, the swing tool comprises a protrusion with means of rotation. The protrusion is located on the first cantilevered end of the swing tool, and the means of rotation are configured to allow a rotational movement of the load cell in relation to the swing tool.

Advantageously, the means of rotation allow the rotational movement of the load cell in relation to the swing tool, in such a way that the means of rotation facilities the movement of the swing tool in relation to the movement of the actuator and the load cell.

In a particular embodiment, the horizontal bar element comprises a kinematic guide joined to the load cell. The kinematic guide is configured to move horizontally along the horizontal bar element continually in contact with the load cell.

Advantageously, the motor allows the movement of the kinematic guide along the horizontal bar element. Additionally, the motor is responsible for applying a force on the swing tool by the actuator. Both movements allow a correct and accurate positioning of the load cell in relation to the swing tool.

In a particular embodiment, the horizontal bar element comprises a guiding cavity. In a more particular embodiment, the swing tool further comprises a second cantilevered end being parallel to the first cantilevered end, and a guiding bar. In a more particular embodiment, the first and second cantilevered end are linked through the guiding cavity of the horizontal element by the guiding bar, such guiding bar being configured to slide along the guiding cavity.

In a particular embodiment, the actuator is configured to apply a compression force on the cantilevered end of the swing tool.

In another particular embodiment, the actuator further comprises at least one beam fixed to the support end of the swing tool and located in contact with the load cell.

Advantageously, the beam fixed to the support end of the swing tool allows the force applied by the actuator to be appropriately transmitted to the swing tool.

In a particular embodiment, the horizontal bar element and the at least one beam comprise at least two rotational elements. The rotational elements are linked to the load cell, and they are configured to allow a rotational movement of the load cell in relation to the horizontal bar element and to at least the beam.

In another particular embodiment, the actuator further comprises at least one beam fixed to the support end of the swing tool and fixed to the horizontal bar element by rotational elements. The rotational elements are configured to allow a rotational movement of the beam in relation to the horizontal bar element.

In a particular embodiment, the actuator is configured to apply traction force on the support end of the swing tool.

Advantageously, the rotational elements are arranged for allowing the movement of the load cell in relation to the beam and the horizontal bar element due to the action of the actuator of applying traction force on the swing tool.

In a particular embodiment, the system further comprises at least a second fixing means configured to fix the actuator to the first element.

Advantageously, the first fixing means allows keeping the actuator fixed to the first element, in such a way that during the action of applying a force on the swing tool, the actuator is prevented from moving on the first element.

Advantageously, the second fixing means allows the support end of the swing tool to remain fixed relative to the second element, in such a way that during the action of applying a force on the swing tool, due to the fixing, the second element is detached from the first element.

In a particular embodiment, the first curved side of the swing tool comprises a range between 75-500 mm.

In a second inventive aspect, the invention provides a method for testing bonded joints, the bonded joints comprising:
 a first element,
 a second element, and
 an adhesive line located between the first and second element,
 wherein the first and second element are joined together by the adhesive line, and the first and second element comprise an end side free of adhesive line between both elements,
 the method comprising the steps of:
 a) providing a system for testing bonded joints according to the first inventive aspect,
 b) fixing the swing element to the second element by the first fixing means,
 c) operating the actuator, applying a force on the swing tool separating the second element from the first element, and
 d) measuring the force applied on the swing tool by the pressure measuring means.

The resulting force that the pressure measuring means measures is proportional to the force that the actuator applies to the swing tool, only in the case where the relative forces between the actuator and the swing tool are constant.

In a particular embodiment, the method further comprises a step of fixing the actuator to the first element by the second fixing means prior to the step c).

In a particular embodiment, the method further comprises a step of wherein a release film is located in the end side of the bonded joint and joined to the second element, prior to the step a).

All the features described in this specification (including the claims, description and drawings) and/or all the steps of the described method can be combined in any combination, with the exception of combinations of such mutually exclusive features and/or steps.

BRIEF DESCRIPTION OF THE DRAWINGS

These and other characteristics and advantages of the invention will become clearly understood in view of the detailed description of the invention which becomes apparent from a preferred embodiment of the invention, given just as an example and not being limited thereto, with reference to the drawings.

FIG. 3B shows a lateral view of the system in a second position, applying force on the swing tool, according to a particular embodiment of the present invention.

FIG. 4 shows a lateral view of the system in a second position, applying force on the swing tool, according to another particular embodiment of the present invention.

FIG. 5A shows a perspective view of the system in a first position according to a particular embodiment of the present invention.

FIGS. 5B-5C show a lateral view of the FIG. 4A in a first and second positioned respectively according to a particular embodiment of the present invention.

DETAILED DESCRIPTION OF THE PREFERRED EMBODIMENTS

Figure 1A:
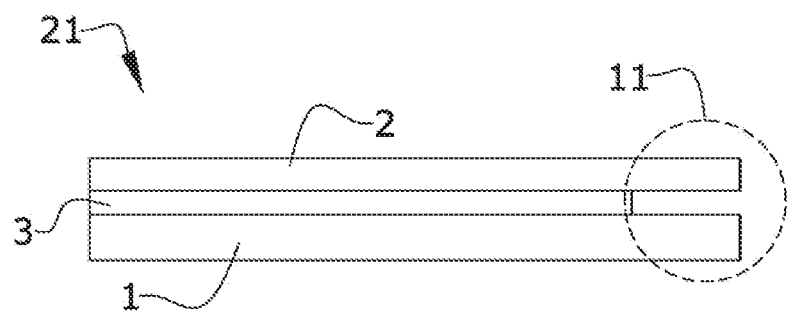
FIGS. 1A-1B show a bonded joint to be tested according to the present invention.
Figure 1B:
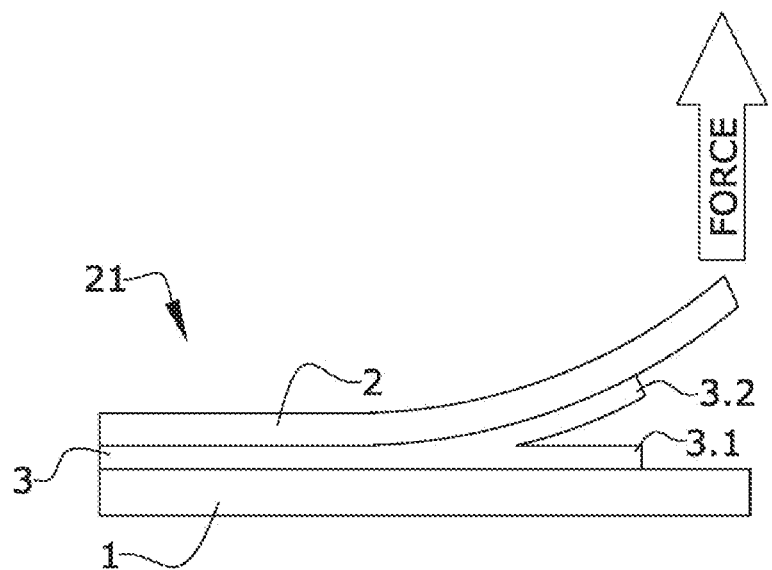

FIGS. 1A and 1B show a bonded joint (21) that comprises a first element (1), a second element (2), and an adhesive line (3) located between the first (1) and second (2) element, in such a way that the first (1) and second (2) element are joined together by the adhesive line (3). The first element (1) comprises a thickness greater than the thickness of the second element (2). Furthermore, the first (1) and second (2) elements comprise between them an end side (11) free of an adhesive line (3). This end side (11) free of an adhesive line allows a better positioning of a first fixing means (14) (not shown) in order to collaborate with the separation of the second element (2) to the first element (1).

In a particular example, the first element (1) is a real part already fabricated of composite materials, and second element (2) element is a test of composite materials.

FIG. 1B shows the second element (2) substantially separated from the first element (1) due to a force applied on the end side (11). In such a way, the second element (2) is not completely separated from the first element (1) and the adhesive line is divided in a first (3.1) and second (3.2) adhesive line part, thus the first (3.1) and second (3.2) adhesive line parts remain bonded to the first (1) and second (2) elements respectively (also shown in FIGS. 2B, 3B and 4).

FIGS. 2A-5C show a system (20) that comprises a swing tool (4), an actuator (5), and pressure measuring means (6).

The actuator (5) is configured to apply a force on the swing tool (4) in order to separate the second element (2) with respect to the first element (1).

The swing tool (4) comprises a first curved side (4.1) configured to be located about the second element (2) and configured to swing on the second element (2). The swing tool (4) further comprises a first cantilevered end (4.2) and a support end (4.3).

The actuator (5) comprises a motor (7) with an axis (8), and the motor (7) is configured to supply power the actuator (5). The actuator (5) further comprises a horizontal bar element (9) configured to move vertically along the axis (8) by the motor (7).

FIGS. 2A-4 show a release film (12) located on the end side (11) of the bonded joints (21) and joined to the second element (2). In this way, the first fixing means (14) which is located on the support end (4.3) of the swing tool (4), fixes the swing tool (4) to the second element (2) and the release film (12). The release film (12) is arranged in the end side (11) in order to prevent the adhesive line (3) from flowing between the first (1) and second (2) elements. In a particular example, the release film (12) extends 50 mm lengthwise between the first (1) and second (2) element.

Furthermore, it is shown that the system (20) comprises a first fixing means (14) configured to fix the swing tool (4) to the second element (2), and a second fixing means (13) configured to fix the actuator (5) to the first element (1).

The end side (11) of the bonded joints (21) is provided in order to facilitate the fixing between the swing tool (4) and the second element (2) by the first fixing means (14).

In a particular example, the fixing means (13, 14) are U-shaped structural elements with an attachment means (19). The U-shaped structural elements (not shown) comprise a first fixing part (13.1, 14.1), a central fixing part (13.2, 14.2) and a second fixing part (13.3, 14.3). In this particular example, the second fixing part (13.3, 14.3) is configured to be located under the first element (1) and the second element (2) respectively, and the U-shaped structural elements are fixed to the actuator (5) and to the swing tool (4) by the fastener (19). In a more particular example, the second fixing part (13.3, 14.3) comprises a rectangular shape, and the attachment means (19) are fasteners.

FIGS. 2A-3B show a system (20) wherein the pressure measuring means (6) is a load cell located in contact with the swing tool (4) and the actuator (5).

Figure 2A:
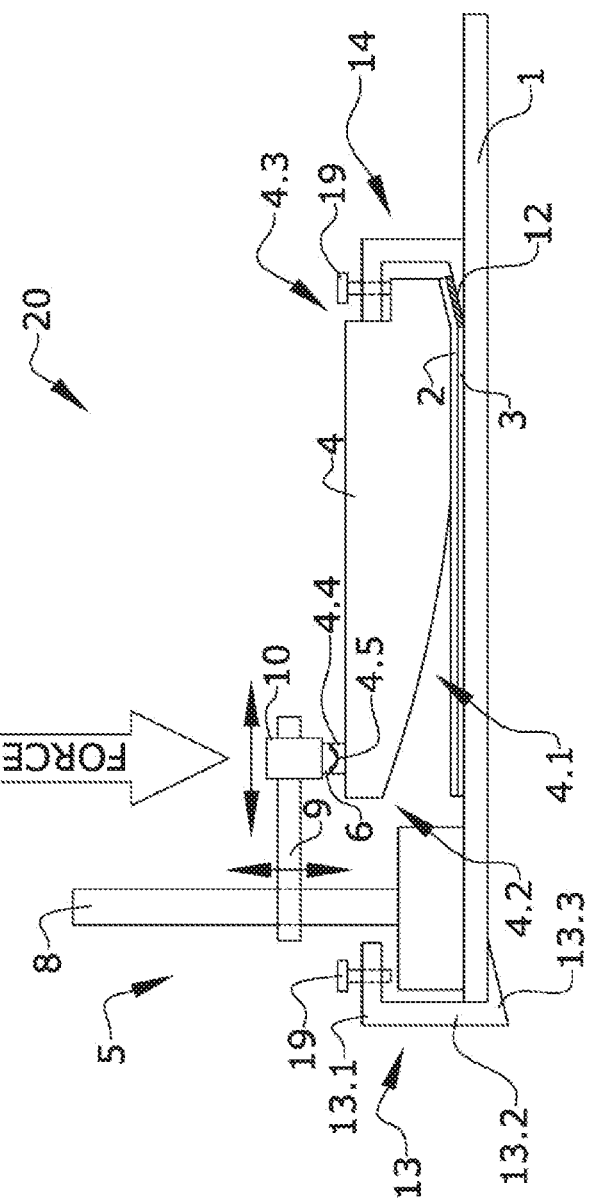
FIG. 2A shows a lateral view of the system in a first position according to a particular embodiment of the present invention.
Figure 2B:
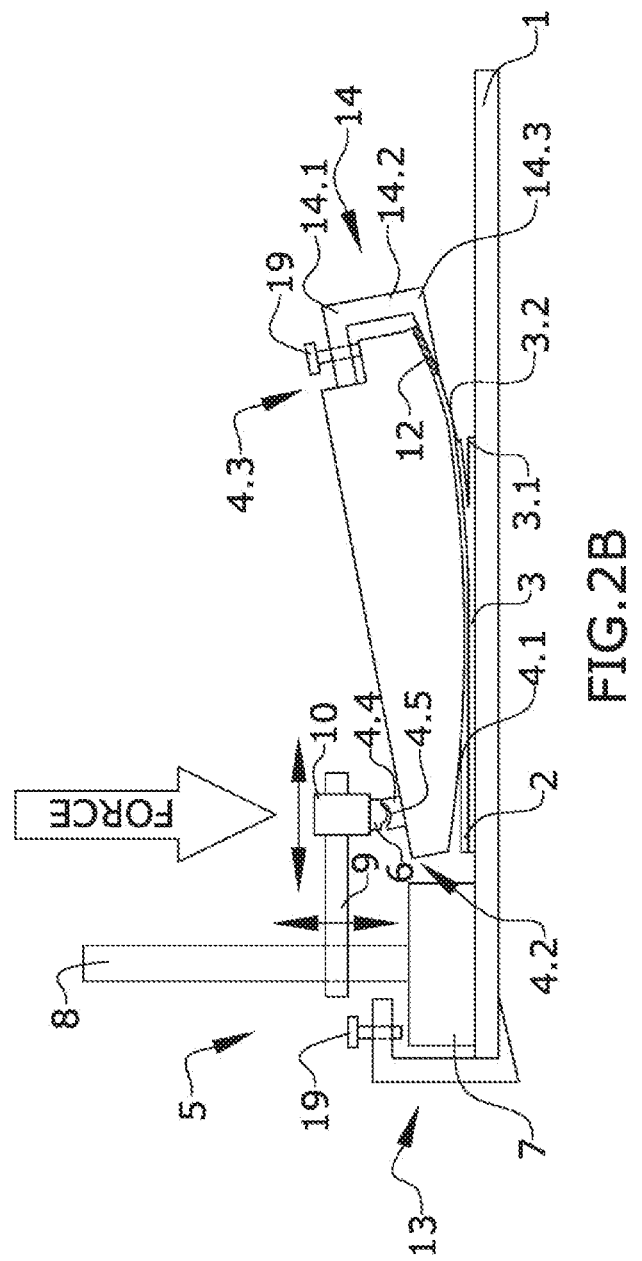
FIG. 2B shows a lateral view of the system in a second position, applying force on the swing tool, according to a particular embodiment of the present invention.

FIGS. 2A and 2B show a system (20) wherein the swing tool (4) comprises a protrusion (4.4). The protrusion (4.4) comprises a means of rotation (4.5) and is located on the first cantilevered end (4.2) of the swing tool (4). The means of rotation (4.5) are configured to allow a rotational movement of the load cell (6) in relation to the swing tool (4).

The horizontal bar element (9) comprises a kinematic guide (10) that is located about the load cell (6), and is configured to move horizontally along the horizontal bar element (9), continually being in contact with the load cell (6).

FIG. 2A shows a first position of the system (20) wherein the swing tool (4) is located on the second element (2) of the bonded joint (21), and fixed to the second element (2) by the first fixing means (14). Additionally it is shown that the actuator (5) fixed to the first element (1) of the bonded joint (21). In this first position, the actuator has not applied any force to the swing tool (4).

FIG. 2B shows a second position of the system (20) wherein the actuator (5) is applying a compression force on the cantilever end (4.2) of the swing tool (4), thus the swing tool (4) is swung and the support end (4.3) is elevated together with the second element (2) due to the fixing between the second element (2) and the second fixing means (14). The application of the compression force on the swing tool (4) produces the separation of the second element (2) from the first element (1), and the compression force is measured by the load cell (6) at the same time.

As is shown in FIG. 2B, the motor (7) operates and generates the movement of the horizontal bar element (9) along the axis (8) (in the direction the arrow "FORCE" indicates), and the movement of the kinematic guide (10) along the horizontal bar element (9), and consequently generates a compression force on the swing tool (4) at the same time that the load cell (6) rotates on the means of rotations (4.5).

Figure 3A:
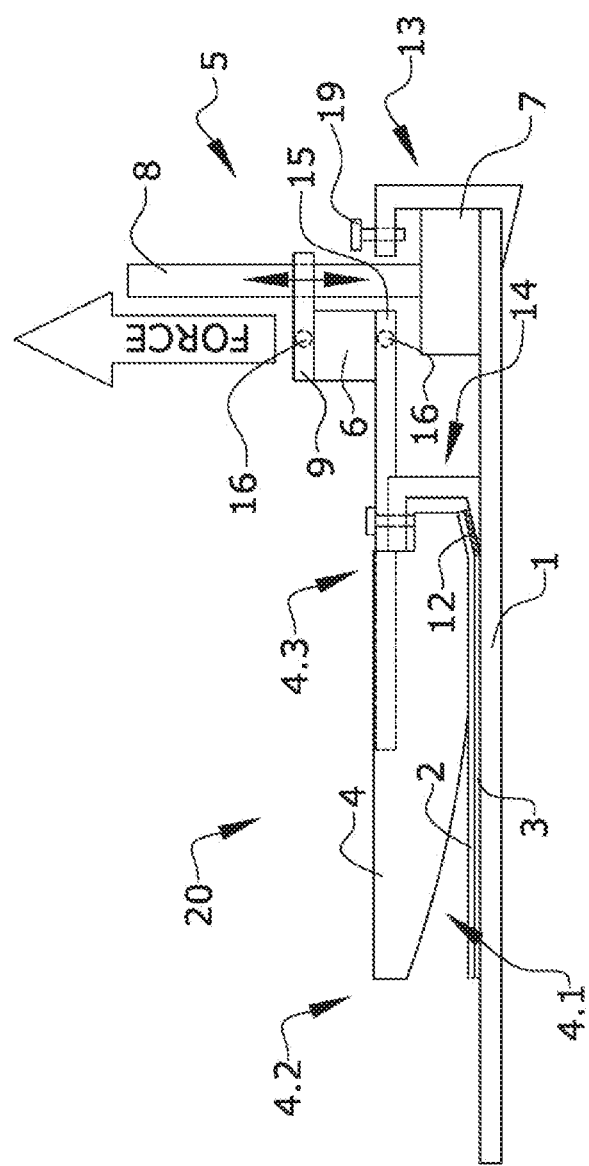
FIG. 3A shows a lateral view of the system in a first position according to a particular embodiment of the present invention.

FIG. 3A shows a first position of the system (20) wherein the actuator (5) further comprises a beam (15) fixed to the support end (4.3) of the swing tool (4) and located in contact with the load cell (6).

The horizontal element (9) and the beam (15) comprise two rotational elements (16) linked to the load cell (6). The rotational elements (16) are configured to allow a rotational movement of the load cell (6) in relation to the horizontal element (9) and the beam (15).

The FIG. 3B shows a second position of the system (20) wherein the actuator (5) is applying a traction force on the support end (4.3) of the swing tool (4), thus the swing tool (4) is swung and the support end (4.3) is elevated together with the second element (2) due to the fixing between the second element (2) and the second fixing means (14). The application of the traction force on the swing tool (4) produces the separation of the second element (2) from the first element (1), and the traction force is measured by the load cell (6) at the same time.

As is shown in FIG. 3B, the motor (7) operates and generates the movement of the horizontal bar element (9) along the axis (8) (in the direction the arrow "FORCE" indicates), and the rotational movement of the beam (15) in relation to the load cell (6) by the rotational elements (16), and consequently generates a traction force on the swing tool (4).

FIGS. 4-5C show a system (20) wherein the pressure measuring means (6) is a load cell located inside the actuator (5).

The FIG. 4 shows a second position of the system (20) wherein the actuator (5) is applying a traction force on the support end (4.3) of the swing tool (4), thus the swing tool (4) is swung and the support end (4.3) is elevated together with the second element (2) due to the fixing between the second element (2) and the second fixing means (14). The application of the traction force on the swing tool (4) produces the separation of the second element (2) from the first element (1), and the traction force is measured by the actuator (5) at the same time.

Furthermore, the motor (7) operates and generates the movement of the horizontal bar element (9) along the axis (8) (in the direction the arrow "FORCE" indicates), and the rotational movement of the beam (15) in relation to the horizontal bar element (9) by the rotational elements (16), and consequently generates a traction force on the swing tool (4).

FIGS. 5A-5C show a particular example of the system (20) wherein the horizontal bar element (9) comprises a guiding cavity (9.1), and wherein the swing tool (4) further comprises a second cantilevered end (4.4) and a guiding bar (4.5). The second cantilevered end (4.4) is parallel to the first cantilevered end (4.2). The first (4.2) and the second (4.5) cantilevered ends are linked through the guiding cavity (9.1)

of the horizontal element (9) by the guiding bar (4.5). The guiding bar (4.5) is configured to slide along the guiding cavity (9.1).

As is shown in FIGS. 5A-5C, the motor (7) operates and generates the movement of the horizontal bar element (9) along the axis (8), and the sliding movement of guiding bar (4.5) along the guiding cavity (9.1) of the horizontal bar element (9), and consequently generates a compression force on the swing tool (4).

FIG. 5A shows a system (20) wherein the swing tool (4) comprises a cavity (4.6) located on a second curved side (4.7) of the swing tool (4). The second curved side (4.7) is located parallel and opposite to the first curved side (4.1) of the swing tool (4). The swing tool (4) comprises the cavity (4.6) in order to allow the horizontal bar (9) to go into the swing tool (4) across the cavity (4.6) when the actuator (5) applies a compression force to the swing tool (4) (as it shown in FIG. 5C).

FIG. 5B shows a system (20) in a first position (the same position shown in FIG. 5A) wherein the support end (4.3) of the swing tool (4) is located in contact with the bonded joints (21).

FIG. 5C shows a system (20) in a second position wherein the guiding bar (4.5) slides along the guiding cavity (9.1) of the horizontal bar element (9) by the application of a compression force of the actuator on the swing tool (4).

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A system for testing bonded joints, the bonded joints comprising:
   a first element,
   a second element, and
   an adhesive line located between the first and second element,
   wherein the first and second element are joined together by the adhesive line, and the first and second element comprise an end side free of an adhesive line between both elements,
   the system comprising:
      a swing tool comprising
         a first curved side configured to be located and swing on the second element,
         a first cantilevered end, and
         a support end,
      an actuator,
      pressure measuring means, and
      a first fixing means configured to fix the swing tool to the second element,
   wherein the actuator is configured to apply a force to the swing tool and configured to separate the second element with respect to the first element,
   wherein the pressure measuring means are configured to measure a force applied by the actuator to the swing tool, and
   wherein the actuator comprises,
      a motor with an axis, the motor being configured to supply power to the actuator, and
      a horizontal bar element configured to move vertically along the axis by the motor.

2. The system according to claim 1 wherein
   the horizontal bar element comprises a guiding cavity, and
   the swing tool further comprises a second cantilevered end being parallel to the first cantilevered end, and a guiding bar,
   wherein the first and second cantilevered ends are linked through the guiding cavity of the horizontal element by the guiding bar, such guiding bar being configured to slide along said guiding cavity.

3. The system according to claim 1, wherein the actuator further comprises, at least one beam fixed to the support end of the swing tool and fixed to the horizontal bar element by rotational elements, said rotational elements being configured to allow a rotational movement of the beam in relation to the horizontal bar element.

4. A system for testing bonded joints, the bonded joints comprising:
   a first element,
   a second element, and
   an adhesive line located between the first and second element,
   wherein the first and second element are joined together by the adhesive line, and the first and second element comprise an end side free of an adhesive line between both elements,
   the system comprising:
      a swing tool comprising
         a first curved side configured to be located and swing on the second element
         a first cantilevered end, and
         a support end,
      an actuator,
      pressure measuring means, and
      a first fixing means configured to fix the swing tool to the second element,
   wherein the actuator is configured to apply a force to the swing tool and configured to separate the second element with respect to the first element,
   wherein the pressure measuring means are configured to measure a force applied by the actuator to the swing tool, and
   wherein the pressure measuring means is at least one of a load cell located inside the actuator or a load cell located in contact with the swing tool and the actuator.

5. The system according to claim 4, wherein the swing tool comprises a protrusion with means of rotation, said protrusion being located on the first cantilevered end of the swing tool, and said means of rotation being configured to allow a rotational movement of the load cell in relation to the swing tool.

6. The system according to claim 4, wherein the horizontal bar element comprises a kinematic guide joined to the load cell, said kinematic guide being configured to move horizontally along the horizontal bar element continually in contact with the load cell.

7. The system according to claim 4, wherein the actuator further comprises at least one beam fixed to the support end of the swing tool and located in contact with the load cell.

8. The system according to claim 7, wherein the horizontal bar element and the at least one beam comprise at least two rotational elements, said rotational elements being linked to the load cell and being configured to allow a rotational movement of the load cell in relation to the horizontal bar element and the at least one beam.

9. The system according to claim 7, wherein the actuator is configured to apply traction force on the support end of the swing tool.

10. A system for testing bonded joints, the bonded joints comprising:
   a first element,
   a second element, and
   an adhesive line located between the first and second element,
   wherein the first and second elements are joined together by the adhesive line, and the first and second elements comprise an end side free of an adhesive line between both elements,
the system comprising:
   a swing tool comprising
      a first curved side configured to be located and swing on the second element,
      a first cantilevered end, and
      a support end,
   an actuator,
   pressure measuring means, and
   a first fixing means configured to fix the swing tool to the second element,
   wherein the actuator is configured to apply a force to the swing tool and configured to separate the second element with respect to the first element,
   wherein the pressure measuring means are configured to measure a force applied by the actuator to the swing tool, and
   wherein the actuator is configured to apply a compression force on the first cantilevered end of the swing tool.

11. A system for testing bonded joints, the bonded joints comprising:
   a first element,
   a second element, and
   an adhesive line located between the first and second element,
   wherein the first and second element are joined together by the adhesive line, and the first and second element comprise an end side free of an adhesive line between both elements,
the system comprising:
   a swing tool comprising
      a first curved side configured to be located and swing on the second element
      a first cantilevered end, and
      a support end,
   an actuator,
   pressure measuring means, and
   a first fixing means configured to fix the swing tool to the second element,
   wherein the actuator is configured to apply a force to the swing tool and configured to separate the second element with respect to the first element,
   wherein the pressure measuring means are configured to measure a force applied by the actuator to the swing tool, and
   at least a second fixing means configured to fix the actuator to the first element.

12. A method for testing bonded joints, the bonded joints comprising:
   a first element,
   a second element, and
   an adhesive line located between the first and second element,
   wherein the first and second element are joined together by the adhesive line, and the first and second element comprise an end side free of an adhesive line between both elements,
the method comprising the steps of:
   providing a system for testing bonded joints according to claim 1,
   fixing the swing element to the second element by the first fixing means,
   operating the actuator,
   applying a force on the swing tool separating the second element from the first element,
   measuring the force applied on the swing tool by the pressure measuring means,
   fixing the actuator to the bonded joint by the second fixing means prior to operating the actuator.

* * * * *